United States Patent
Balaji et al.

(10) Patent No.: US 11,950,900 B2
(45) Date of Patent: Apr. 9, 2024

(54) METHOD AND SYSTEM FOR FRAILTY DETECTION

(71) Applicant: Tata Consultancy Services Limited, Mumbai (IN)

(72) Inventors: Ramesh Balaji, Chennai (IN); Srinivasa Raghavan Venkatachari, Chennai (IN); Anirudh Thenguvila Purushothaman, Kochi (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 241 days.

(21) Appl. No.: 17/353,920

(22) Filed: Jun. 22, 2021

(65) Prior Publication Data

US 2021/0401328 A1 Dec. 30, 2021

(30) Foreign Application Priority Data

Jun. 24, 2020 (IN) .............................. 202021026765

(51) Int. Cl.
*A61B 5/11* (2006.01)
*G01C 22/00* (2006.01)
*G16H 50/30* (2018.01)

(52) U.S. Cl.
CPC ........... *A61B 5/1118* (2013.01); *A61B 5/1113* (2013.01); *G01C 22/006* (2013.01); *G16H 50/30* (2018.01); *A61B 2560/04* (2013.01); *A61B 2562/0233* (2013.01)

(58) Field of Classification Search
CPC . A61B 5/1118; A61B 5/1113; A61B 2560/04; A61B 2562/0233; G01C 22/006; G16H 20/70; G16H 50/30
See application file for complete search history.

(56) References Cited

U.S. PATENT DOCUMENTS

2014/0107932 A1* 4/2014 Luna ...................... G16H 50/20
702/19

OTHER PUBLICATIONS

Stavrotheodoros, Stefanos, et al. "A Smart-Home IoT Infrastructure for the Support of Independent Living of Older Adults" 2018, IFIP, 238-249. (Year: 2018).*
Goonawardene, Nadee, et al. "Unobtrusive Detection of Frailty in Older Adults" 2018, Springer Nature, 290-302 (Year: 2018).*
Jiang, Chuan "A Smart and Minimum-Intrusive Monitoring Framework Design for Health Assessment of the Elderly" 2015, University of Cincinatti (Year: 2015).*

(Continued)

*Primary Examiner* — Rene T Towa
*Assistant Examiner* — Anna Roberts
(74) *Attorney, Agent, or Firm* — FINNEGAN, HENDERSON, FARABOW, GARRETT & DUNNER LLP

(57) ABSTRACT

Elderly people suffer from health issues, and timely detection can save lives. State of the art techniques either make certain assumptions or require clinical data in order to perform the frailty detection, which affects the quality as well as cause inconvenience to the users. The disclosure herein generally relates to patient monitoring and, more particularly, to frailty detection using pedometer sensor data, PIR sensor data, and door sensor data. The system determines activity levels of the user being monitored, based on data from the pedometer sensors, PIR sensors, and door sensors, and based on the determined activity levels, further determines whether the user has frailty or not.

20 Claims, 4 Drawing Sheets

(56) References Cited

OTHER PUBLICATIONS

Hulya Gokalp et al., "Integrated telehealth and telecare for monitoring frail elderly with chronic disease", Telemedicine and e-Health, Aug. 2018, vol. 24 (12), National Library of Medicine, https://www.researchgate.net/publication/327150330_Integrated_Telehealth_and_Telecare_for_Monitoring_Frail_Elderly_with_Chronic_Disease/link/5eb1a0a045851592d6bb07f0/download.

Nadee Goonawardene et al., "Unobtrusive detection of frailty in older adults", International Conference on Human Aspects of IT for the Aged Population, Jun. 2018, Springer, https://ink.library.smu.edu.sg/cgi/viewcontent.cgi?article=5100&context=sis_research.

Joaquim Bellmunt Montoya, "Modeling human behaviors and frailty for a personalized ambient assisted living framework," Modeling human behaviors and frailty for a personalized ambient assisted living framework, Dec. 2018, HAL, https://tel.archives-ouvertes.fr/tel-01955485/document.

Javad Razjouyan et al., "Wearable sensors and the assessment of frailty among vulnerable older adults: An observational cohort study", Sensors, Apr. 2018, MDPI, https://www.mdpi.com/1424-8220/18/5/1336.

\* cited by examiner

METHOD AND SYSTEM FOR FRAILTY DETECTION

PRIORITY CLAIM

This U.S. patent application claims priority under 35 U.S.C. § 119 to: India Application No. 202021026765, filed on Jun. 24, 2020. The entire contents of the aforementioned application are incorporated herein by reference.

TECHNICAL FIELD

This disclosure relates generally to patient monitoring, and more particularly to frailty detection using pedometer sensor data, PIR sensor data, and door sensor data.

BACKGROUND

The elderly population suffers from various health problems, and many of them live independently. Early detection of diseases and treatment helps in saving many lives. Frailty, which is a condition of being weak, is a common situation that a majority of the elder people are in. However, this frailty may be indicative of various other diseases as well. As a result, detection of frailty in the elder people may help ensure that timely treatment is provided to them, and this in turn may help avoid many situations which would have happened otherwise.

The inventors here have recognized several technical problems with such conventional systems, as explained below. Many systems exist which can perform the patient monitoring for frailty detection. Some of these existing systems rely on clinical data. However, one disadvantage with such approaches is that frequent clinical data collection for monitoring health of the user may inconvenience. Approaches being used by different systems also may vary from one another, in terms of types of information collected, the approach used for processing the collected data and so on. Some of the state of the art systems may make certain assumptions during the monitoring. For example, a system may be configured to believe that if a person being monitored stays inside a room for a certain time period, say 30 minutes, the user is sleeping. This may not be true always, and can lead to false results.

SUMMARY

Embodiments of the present disclosure present technological improvements as solutions to one or more of the above-mentioned technical problems recognized by the inventors in conventional systems. For example, in one embodiment, a processor implemented method for frailty detection is provided. In this method, initially a Passive Infrared (PIR) sensor data and door sensor data are obtained, from a plurality of PIR sensors and door sensors respectively, positioned at different locations of a building where a user being monitored is located, as a first input via one or more hardware processors. Further, pedometer data with respect to movement of the user is obtained as a second input, via the one or more hardware processors, using one or more pedometer sensors. Further, the PIR sensor data and the door sensor data are processed to generate a room movement data model, a day-time bedroom-stay data model, and an outdoor home movement model, for the user, via the one or more hardware processors. Further, the pedometer data is processed to generate a user activity model for the user, via one or more hardware processors. Further, weights are assigned to one or more data points deduced from the room movement data model, the day-time bedroom stay data model, the outdoor home movement model, and the user activity model, and then a weighted cumulative percentage value is calculated for each of the one or more data points, based on the assigned weights and measured value of each of the one or more data points. Further, a cumulative frailty percentage value is calculated based on the weighted cumulative percentage value of the one or more data points. Further, the user being monitored is determined as having frailty if the cumulative frailty percentage value exceeds a frailty threshold.

In another aspect, a system for frailty detection is provided. The system includes one or more hardware processors, a communication interface, and a memory storing a plurality of instructions. The plurality of instructions when executed cause the one or more hardware processors to obtain Passive Infrared (PIR) sensor data and door sensor data, from a plurality of PIR sensors and door sensors respectively, positioned at different locations of a building where a user being monitored is located, as a first input. The system further obtains pedometer data with respect to movement of the user as a second input, via the one or more hardware processors, using one or more pedometer sensors. The system then processes the PIR sensor data and the door sensor data to generate a room movement data model, a day-time bedroom-stay data model, and an outdoor home movement model, for the user, via the one or more hardware processors. The system then generates a user activity model for the user, by processing the pedometer data via one or more hardware processors. The system then assigns weights to one or more data deduced from the room movement data model, the day-time bedroom stay data model, the outdoor home movement model, and the user activity model, and then a weighted cumulative percentage value is calculated for each of the one or more data points, based on the assigned weights and measured value of each of the one or more data points. The system further calculates a cumulative frailty percentage value is calculated based on the weighted cumulative percentage value of the one or more data points. Further, the system determines the user being monitored as having frailty if the cumulative frailty percentage value exceeds a frailty threshold.

In yet another aspect, a non-transitory computer readable medium for frailty detection is provided. The non-transitory computer readable medium is comprised of a plurality of instructions, which when executed, case one or more hardware processors to perform the following method for frailty detection. In this method, initially Passive Infrared (PIR) sensor data and door sensor data are obtained, from a plurality of PIR sensors and door sensors respectively, positioned at different locations of a building where a user being monitored is located, as a first input via one or more hardware processors. Further, pedometer data with respect to movement of the user is obtained as a second input, via the one or more hardware processors, using one or more pedometer sensors. Further, the PIR sensor data and the door sensor data are processed to generate a room movement data model, a day-time bedroom-stay data model, and an outdoor home movement model, for the user, via the one or more hardware processors. Further, the pedometer data is processed to generate a user activity model for the user, via one or more hardware processors. Further, weights are assigned to one or more data points deduced from the room movement data model, the day-time bedroom stay data model, the outdoor home movement model, and the user activity model, and then a weighted cumulative percentage value is calculated for each of the one or more data points, based on the assigned weights and measured value of each of the one or more data points. Further, a cumulative frailty percentage value is calculated based on the weighted cumulative percentage value of the one or more data points. Further, the user being monitored is determined as having frailty if the cumulative frailty percentage value exceeds a frailty threshold.

In yet another aspect, a non-transitory computer readable medium for frailty detection is provided. The non-transitory computer readable medium is comprised of a plurality of instructions, which when executed, case one or more hardware processors to perform the following method for frailty detection. In this method, initially a Passive Infrared (PIR) sensor data and door sensor data are obtained, from a plurality of PIR sensors and door sensors respectively, positioned at different locations of a building where a user being monitored is located, as a first input via one or more hardware processors. Further, a pedometer data with respect to movement of the user is obtained as a second input, via the one or more hardware processors, using one or more pedometer sensors. Further, the PIR sensor data and the door sensor data are processed to generate a room movement data model, a day-time bedroom-stay data model, and an outdoor home movement model, for the user, via the one or more hardware processors. Further, the pedometer data is processed to generate a user activity model for the user, via one or more hardware processors. Further, weights are assigned to one or more data points deduced from the room movement data model, the day-time bedroom stay data model, the outdoor home movement model, and the user activity model, and then a weighted cumulative percentage value is calculated for each of the one or more data points, based on the assigned weights and measured value of each of the one or more data points. Further, a cumulative frailty percentage value is calculated based on the weighted cumulative percentage value of the one or more data points. Further, the user being monitored is determined as having frailty if the cumulative frailty percentage value exceeds a frailty threshold.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Figure 1:
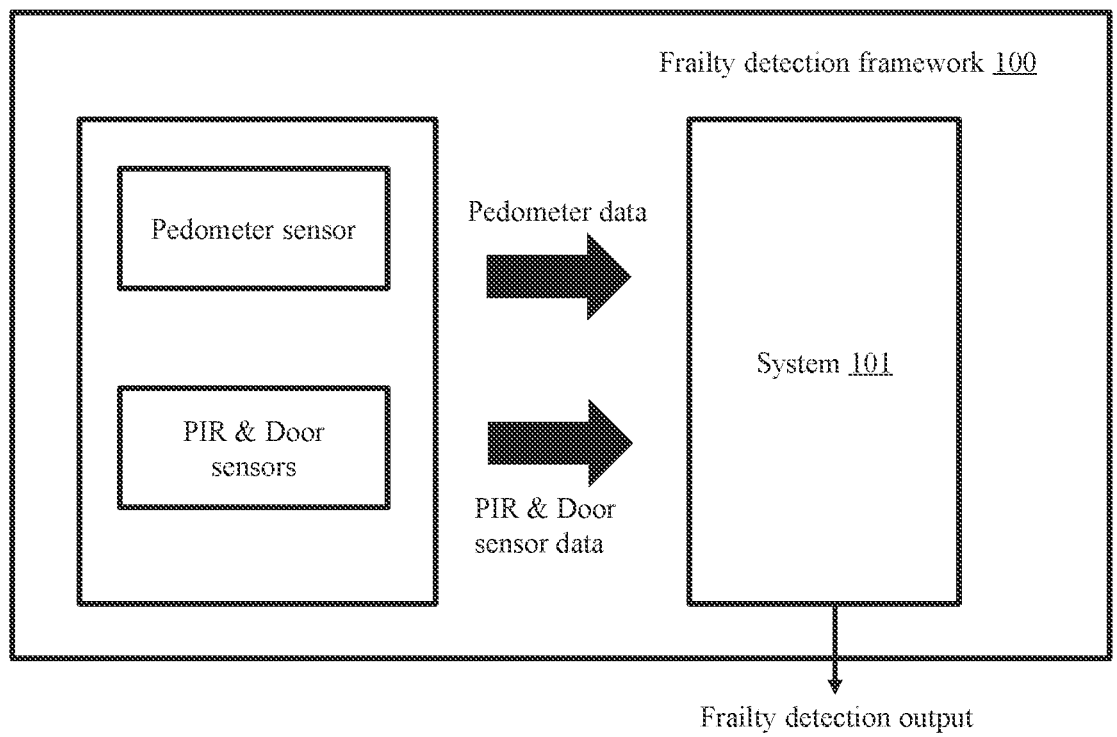
FIG. 1 illustrates an exemplary block diagram of a frailty detection framework for frailty detection, according to some embodiments of the present disclosure.

FIG. 1 illustrates an exemplary block diagram of a frailty detection framework for frailty detection, according to some embodiments of the present disclosure. The frailty detection framework 100 is configured to perform the frailty detection of a user, based on movements of the user between rooms of a building the user is located at, and movements of the user out of the building. For explaining the process, the building is considered as home of the user. The frailty detection framework 100 includes a system 101, one or more pedometer sensors, one or more Passive Infrared (PIR) sensors, and one or more door sensors.

The pedometer sensors collect information on counts of steps being taken by a user being monitored, when the user is on the move. The pedometer sensors may be present in one or more gadgets being attached to the user. For example, the pedometer sensors are present in a wearable gadget (for example, a smartwatch) of the user. The PIR sensors are installed at various selected locations of the house, such that the user's movement in and out of each room (or selected rooms) can be tracked. The door sensors are installed at main door of the house, such that the user's movement can be tracked whenever the user is going out of the house and is coming back in. All the sensors (i.e. the one or more pedometer sensors, one or more Passive Infrared (PIR) sensors, and one or more door sensors) are configured to communicate with the system 101 and transmit the collected information (i.e. the step count and the information on the user movements) to the system 101 in real-time, or at fixed time intervals, as configured. The system 101 is configured to process the data collected from the sensors, and determine whether the user has frailty or not. By processing the collected data, the system 101 may determine and analyze day-time activities and night-time activities performed by the user, and in turn determine whether the user has frailty or not. For the purpose of differentiating the activities as day-time activities and night-time activities, the system 101 may be configured to consider time between 7 AM to 7 PM as day time, and time between 7.01 PM to 6.59 AM as night time, any given day. The timings can be configured as per requirements. Based on the collected sensor information, the system 101 assesses movement of the user within the Home, time spent by the user in a Bedroom from 6 am to 6 pm, and time spent on Outdoors by the user, and based on these parameters, the system 101 further determines the frailty of the user.

Figure 2:
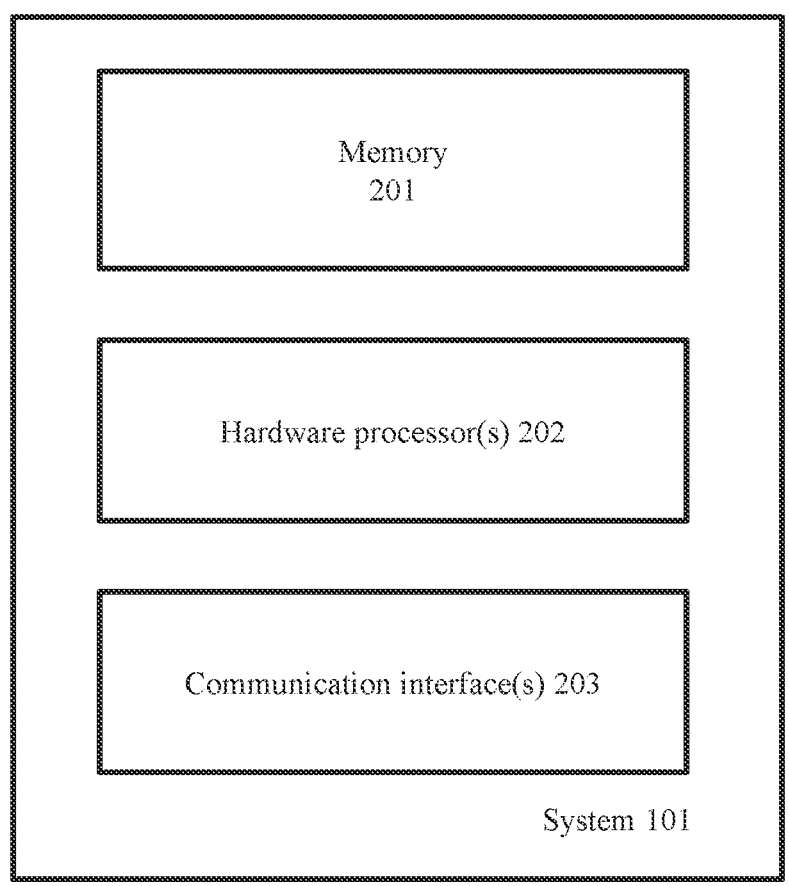
FIG. 2 is a functional block diagram of a system of the frailty detection framework, according to some embodiments of the present disclosure.

FIG. 2 description explains the components of the system 101, and FIG. 3 description, in reference to FIG. 1 and FIG. 2 explains the steps involved in the process of frailty detection being performed by the system 101.

FIG. 2 is a functional block diagram of a system of the frailty detection framework, according to some embodiments of the present disclosure. The system 100 includes one or more hardware processors 202, communication interface(s) or input/output (I/O) interface(s) 203, and one or more data storage devices or memory 201 operatively coupled to the one or more hardware processors 202. The one or more hardware processors 202 can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 101 can be implemented in a variety of computing systems, such as laptop computers, notebooks, hand-held devices, workstations, mainframe computers, servers, a network cloud and the like.

The communication interface(s) 203 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the communication interface(s) 203 can include one or more ports for connecting a number of devices to one another or to another server.

The memory 201 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more components (not shown) of the system 101 can be stored in the memory 201. The memory 201 is configured to store a plurality of operational instructions (or 'instructions') which when executed cause one or more of the hardware processor(s) 202 to perform various actions associated with the code analysis being performed by the system 101. The system 101 can be implemented in a variety of ways as per requirements. Various steps involved in the process of frailty detection being performed by the system 101 are explained with description of FIG. 3. All the steps in FIG. 3 are explained with reference to the system of FIG. 2.

Figure 3A:
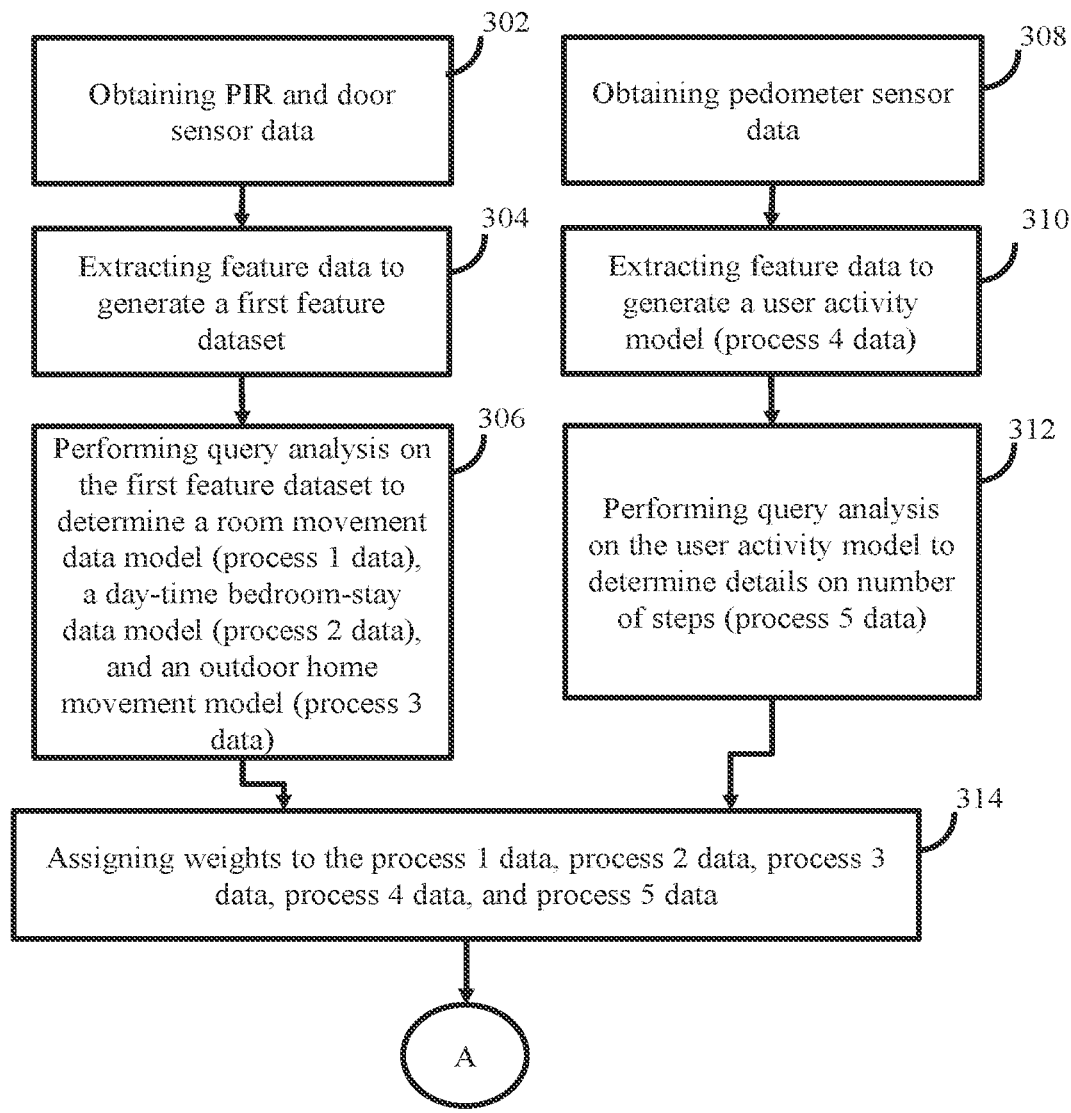
FIGS. 3A and 3B (collectively referred to as FIG. 3 and method 300) illustrate steps involved in the process of frailty detection by the system of FIG. 2, in accordance with some embodiments of the present disclosure.
Figure 3B:
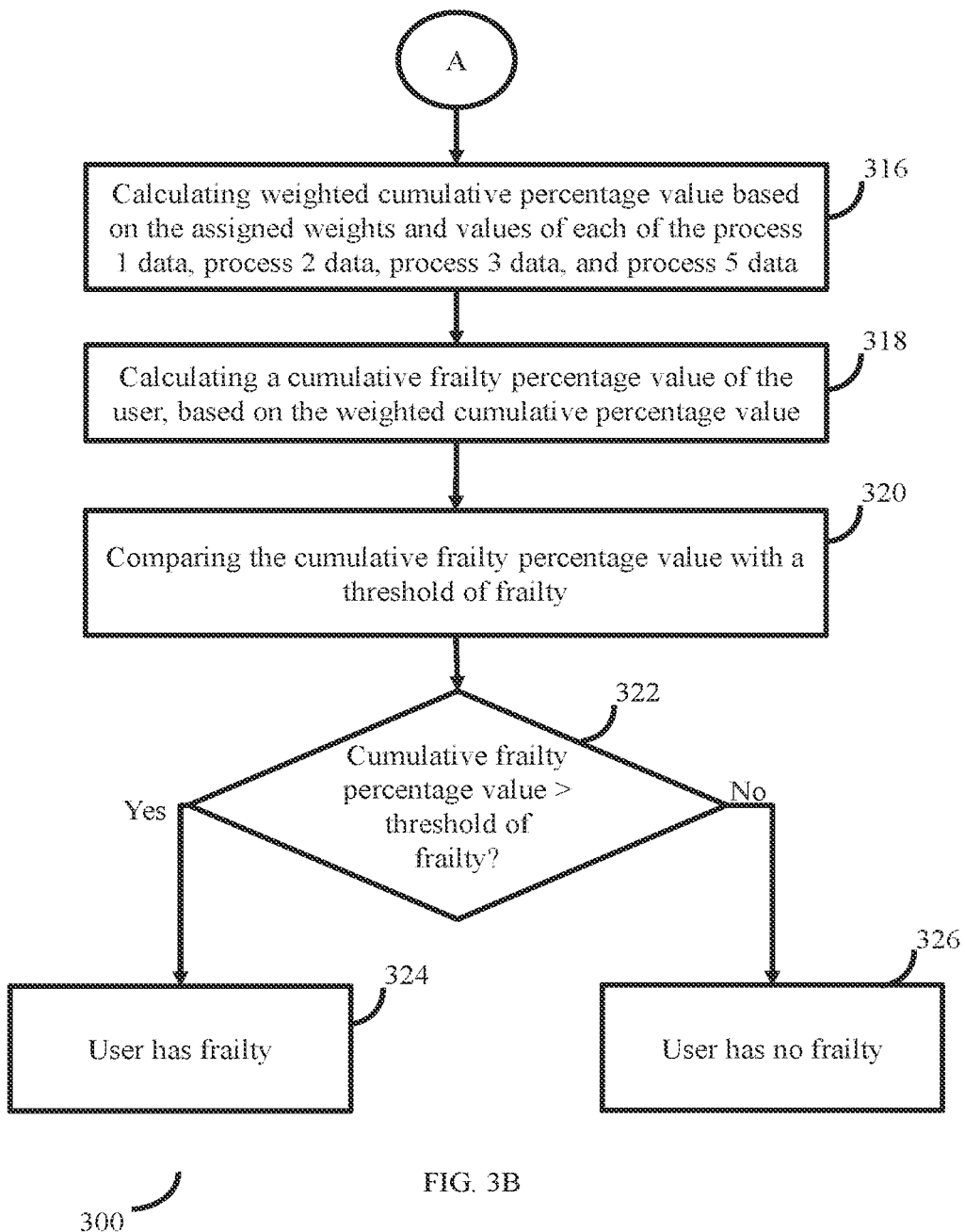

FIGS. 3A and 3B (collectively referred to as FIG. 3 and method 300) illustrate steps involved in the process of frailty detection by the system 101 of FIG. 2, in accordance with some embodiments of the present disclosure. The system 101 obtains (302) the PIR and door sensor data as a first input.

The system 101 also obtains (308) the pedometer sensor data, as a second input. In an embodiment, the system 101 obtains the first input and the second input, simultaneously. At step 304, the system 101 processes the raw PIR and door sensor data collected as input at step 302 to extract feature data to generate a first feature dataset.

TABLE 1

| observation_timestamp | sensor_id | observation_value | resident_id | location |
|---|---|---|---|---|
| 10/31/2018 15:08 | ADS1**** | Yes | AXXXX | LivingRoom |
| 10/31/2018 15:10 | ADS2**** | No | AXXXX | Bedroom |
| 10/31/2018 15:11 | ADS3**** | Yes | AXXXX | Kitchen |
| 10/31/2018 15:12 | ADS4**** | Yes | AXXXX | Bed |

A few examples of feature data that are extracted by the system 101 from the raw sensor data input are given in Table. 1. Based on the extracted data, the system 101 generates the feature dataset, the feature dataset may comprise one or more of ObservationTS, ResidentID, Date, Hour, Minute, Second, Day, Week, Month, Year, Weeday/Weekend, From Location, Tolocation, Timespent, RoomChangeIndicator, "Daytime (Y|N)", "Timeperiod" i.e. whether it is morning 6.00 am to 9.00 pm or Afternoon 3.00 pm to 6.00 pm, and so on. Such data collected over a period of time provides information on where the user spent time over a period of time. An example of the first few columns of feature dataset is given in Table. 2.

TABLE 2

| observation_timestamp | resident_id | Month | Day of the week | Hour | Minute | From_location | To_Location | RoomchangeInd | TimePeriod |
|---|---|---|---|---|---|---|---|---|---|
| 10/31/2018 15:08 | AXXXX | 1 | 4 | 3 | 28 | Bedroom_master | Bedroom_master | N | E9to6 |
| 10/31/2018 15:10 | AXXXX | 1 | 4 | 3 | 29 | Bedroom_master | Living_room | Y | E9to6 |
| 10/31/2018 15:11 | AXXXX | 1 | 4 | 3 | 30 | Living room | Kitchen | Y | E9to6 |
| 10/31/2018 15:12 | AXXXX | 1 | 4 | 3 | 31 | Kitchen | Toilet_room | Y | E9to6 |

The first feature dataset may also contain additional information such as but not limited to a room change indicator (Y/N) which, time difference (in seconds, or minutes, or hours, as pre-configured), weekend/weekday, and so on. If the From location and To location are 'Bedroom_master' over a period of time, then that means the user remained in the master bedroom over that time period, and the room change indicator would be 'N'. Similarly if the From location is 'Living room' and To location is 'Kitchen' over a period of time, then that means the user moved from the Living Room to the Kitchen over that time period, and the room change indicator would be 'Y'. In order to track whether the user is moving out of the house, another parameter 'door' location could be used. An algorithmic representation of the process of generating the first feature dataset is given as:

Sum of Raw Sensor Data for "n" number of days:

$$X\_SRn = XSRd1 + XSRd2 + XSRd3 + \ldots XSRdn$$

Where,

X stands for input.

XSRd1 refers to sensor input for day 1

X_SRn is sum of all sensor inputs from day 1 to n days.

X_SRn is input to Feature Engineering function (FE_func) which gives a Featured Engineered Sensor Output (Z_fesd)

$$Z\_fesd = FE\_func(X\_SRn)$$

Z_fesd, is termed as the first feature dataset, and can be used to build:
a room movement data model,
a day-time bedroom stay data model, and
an outdoor home movement data model Steps involved in building each of the aforementioned data models is given below:

1) Room Movement Data Model (Process 1 Data):

Whenever the user moves from one room to another one (for example, from Kitchen to Living room), this movement of the user is considered as a 'room movement'. In Zjesd, the room change indicator represents the room movement of the user. In order to get information on the room movement, the system 100 queries at step 306) the first feature dataset. The following query is used:

RoomChangeInd="Y" & group by Date

RoomChangeInd="Y" & group by Date

This query fetches a resultset which includes information on all the room movements by the user, grouped by date. An example of the resultset generated by the query is given in Table.3.

TABLE 3

| Date | RoomChangeCounts |
| --- | --- |
| Apr. 1, 2018 | 13 |
| Apr. 2, 2018 | 54 |
| Apr. 3, 2018 | 22 |
| Apr. 4, 2018 | 28 |

This resultset of this query as termed as 'ResultRoomMovement'. The system 101 then calculates a median of a RoomChangeCounts feature of the ResultRoomMovement. Median is selected because it is less susceptible to data noise. Further, the system 101 calculates an average room movement count as:

AvgRoomMovement=median(ResultRoomMovement:RoomChangeCounts)

The system 101 further calculates a Total Count of the RoomChangeCounts feature from the ResultRoom Movement as:

TotalCountRoomMovement=count(ResultRoomMovement:RoomChangeCounts)

The system 101 then calculates value of ReducedRoomChangeAverageCounts, which helps the system 101 in determining how much change has happened in the room movements, and specifically to determine whether there is a decrease in room movement of the user, based on number of instances of the room movement. The system 101 is configured to interpret reduced room movement over a period of time as an indication of the user being weak and not being active. The system 101 calculates the value of ReducedRoomChangeAverageCounts as:

ReducedRoomChangeAverageCounts=ResultRoomMovement:RoomChangeCounts<AvgRoomMovement While calculating the value of ReducedRoomChangeAverageCounts, the system 101 checks, for each date, whether the corresponding room movement count is below the average room movement, and the result is captured. An example of result resultset of the ReducedRoomChangeAverageCounts is given in Table. 4.

TABLE 4

| Date | RoomChangeCounts |
| --- | --- |
| Apr. 1, 2018 | 13 |
| Apr. 2, 2018 | 54 |
| Apr. 3, 2018 | 22 |
| Apr. 4, 2018 | 28 |
| Apr. 5, 2018 | 15 |

Further, the system 101 calculates value of ReducedRoomMovementCount as:

ReducedRoomMovementCount=count (ReducedRoomChangeAverageCounts:RoomChangeCounts)

The system 101 further determines percentage reduction in the Roomchange movement of the user as:

GetReducedRoomChangePercentage=(ReducedRoomMovementCount/TotalCountRoomMovement)*100

Reduction in room movement patterns is represented as Z_FR1, which is deduced from the room movement data model using a function FR_RM used for determining reduction in room movement patterns.

$Z\_FR1 = FR\_RM(Z\_FESD)$

2) Day Time Bedroom Stay Data Model (Process 2 Data)

The day time bedroom stay is another parameter which indicates/represents frailty of the user. The 'Day Time Bedroom stay' represents time the user spends in his/her bedroom during the day time. The system 101 interprets that is the user is spending long hours inside the bedroom during the day time, then the user may have frailty. As mentioned earlier, the system 101 is configured to consider time between 6.00 am to 6. pm as the day time. For example, if the user stays in master bedroom from 6.00 am to 8.00 am, the system 101 considers time of 7200 seconds as "Day Time Bedroom stay". The system 101 determines the "Day Time Bedroom stay" based on "FromLocation", "ToLocation", "RoomchangeInd" and "TimePeriod" features from the first feature dataset, by querying the first feature dataset. The query used by the system 101 to obtain this information is give as:

RoomChangeInd="N",
FromLocation="master_bedroom",
ToLocation="master_bedroom", TimePeriod in ["M6to9", "M9to12", "A12to3", "E3to6"] & group by Date.

This query gives a result set with all sensor data with above conditions sorted by Date (each day). The system 101 obtains time (in seconds) the user spent inside the bedroom, on each day over a period the user being monitored. A sample of the 'Day Time Bedroom stay' data is given in Table. 5.

TABLE 5

| Date | BedroomStayinSeconds |
| --- | --- |
| Apr. 2, 2018 | 4707 |
| Apr. 4, 2018 | 1921 |
| Apr. 10, 2018 | 6082 |
| Apr. 11, 2018 | 3981 |

The resultset for Day Time Bedroom stay query is termed as 'ResultDaytimeBedroomStay'

The system 101 calculates median of the BedroomStayinSeconds feature of the ResultDaytimeBedroomStay resultset. Median is selected because it is less susceptible to data noise.

AvgDaytimeBedroomStay=median(ResultDaytime-
BedroomStay: Bedroom StayinSeconds)

The system 101 further calculates the Total Count of the DaytimeBedroomStayCounts feature of the ResultDaytimeBedroomStay resultset as:

TotalCountDaytimeBedroomStay=count(ResultDaytimeBedroomStay: Bedroom StayinSeconds)

Further, the system 101 determines change in pattern of the Bedroom Daytime Stay. By analyzing the change in pattern of the Bedroom Daytime Stay, the system 101 determines if there is an increase in the Daytime Bedroom Stay. The system 101 interprets that if the user is spending more time in the bedroom during the day time, then the user is inactive, and this may be a sign of frailty. The system 101 determines that the user spends excess time inside the bedroom during the daytime, on any given day, if the daytime bedroom stay movement is exceeding AvgDaytimeBedroomStay, and this is represented as:

ExcessDaytimeBedroomStayAverageCounts= ResultDaytimeBedroomStay:
BedroomStayinSeconds>AvgDaytimeBedroomStay Result of checking the excess bedroom stay is captured in the resultsetExcessDaytimeBedroomStayAverageCounts, and a sample is given in Table. 6.

TABLE 6

| Date | BedroomStayinSeconds |
|---|---|
| Apr. 2, 2018 | 4707 |
| Apr. 4, 2018 | 1921 |
| Apr. 10, 2018 | 6082 |
| Apr. 11, 2018 | 3981 |

The system 101 then calculates total count of the increased daytime bedroom stay, which is a feature of the resultset ExcessDaytimeBedroomStayAverageCounts, as:

IncreasedDaytimeBedroomStayCount=count (ExcessDaytimeBedroomStayAverageCounts:BedroomStayinSeconds)

Further the system 101 determines percentage increase in the daytime bedroom stay, as:

GetIncreasedDaytimeBedroomStayPercentage=(IncreasedDaytimeBedroomStayCount/TotalCountDaytimeBedroomStay)*100

Increase in the daytime bedroom stay is represented as Z_FR2, and is obtained by processing data in the Day Time Bedroom Stay data model using a function FR_DBS. FR_DBS refers to finding increase in Daytime bedroom stay, and returns a numerical percentage.

Z_FR2=FR_DBS(Z_FESD)

3) Outdoor Home Movement Model (Process 3 Data)

The system 101 generates the Outdoor home movement model to understand outdoor home movement of the user, i.e. the system 101 determines how many times the user is going outside of the home. The activity of going out of the home may be interpreted by the system 101 as an indication of the user's social movement. For example, if the user is identified as going out of the home, based on data from the door sensor, this is considered as "Outdoor Home Movement". The system 101 detects the Outdoor Home Movement by querying the first feature dataset to get information on "ToLocation" feature. Query that may be used by the system 101 to get the required information for detecting the Outdoor Home Movement is:

ToLocation="Door" & group by Date.

This query provides a resultset with all sensor data with above conditions sorted by Date (each day) number for the given set of data. A sample of the resultset is given in Table.7.

TABLE 7

| Date | DoorMovement |
|---|---|
| Apr. 1, 2018 | 2 |
| Apr. 2, 2018 | 3 |
| Apr. 3, 2018 | 2 |
| Apr. 4, 2018 | 1 |

This resultset is termed as 'ResultDoorMovement'. The system 101 then calculates average door movement as:

AvgDoorMovement=median(ResultDoorMovement:
DoorMovement)

The system 101 then calculates total count of the DoorMovementCounts feature of the ResultDoorMovement resultset, as:

TotalCountDoorMovement=count(ResultDoorMovement:DoorMovement)

The system 101 further determines how much change has happened in the Door movements. By checking the change in door movements, the system 101 assesses whether there is a decrease in door movement. The system 101 is configured to interpret that if there is a decrease in door movement, then the user is less active or inactive, and this in turn is interpreted as an indication of frailty. The system 101 checks if the door movement is less than the average door movement, and if yes, then determines that the door movement is less. This is calculated as:

ReducedDoorMovementAverageCounts=ResultDoorMovement:
DoorMovement<AvgDoorMovement The result is captured in the resultset ReducedDoorMovementAverageCounts, and a sample is given in Table.8.

TABLE 8

| Date | DoorMovement |
|---|---|
| Apr. 1, 2018 | 2 |
| Apr. 2, 2018 | 3 |
| Apr. 3, 2018 | 2 |
| Apr. 4, 2018 | 1 |

The system 101 then calculates a Total Count of the Reduced Door Movement feature of the resultset ReducedDoorMovementAverageCounts, as:

ReducedDoorMovementCount=count (ReducedDoorMovementAverageCounts:DoorMovement)

Further, the system 101 determines percentage reduction of the outside home movement of the user, as:

GetReducedDoorMovementPercentage=(ReducedDoorMovementCount/TotalCountDoorMovement)*100

The percentage reduction of the outside home movement of the user is represented as Z_FR3, and is determined by the system by processing contents of the Outdoor home movement model using a function FR_DM, wherein FR_DM refers to finding Reduction in outdoor movement patterns. FR_DM will return a numerical percentage.

Z_FR3=FR_DM(Z_FESD)

The system 101 tracks walking steps of the user, based on the pedometer data. The system 101 obtains/collects raw pedometer data from the pedometer sensors as input at step 308. At step 310, the system 101 processes the pedometer sensor data and extracts feature data from the pedometer sensor data to generate a user activity model, at step 310. The user activity model includes information on step count of the user. While processing the pedometer sensor data, the system 101 assesses signs of frailty based on movement of the user within the house through number of steps taken.

While processing the pedometer sensor data, the system 101 initially extracts feature data, and further from the extracted feature data, the system 100 generates the user activity model. Dataset of the user activity model is also termed as 'Process 4 data'. Process of generating the second feature dataset i.e. the process 4 data is explained below.

TABLE 9

| objectUniqueId | observationData | observationDate |
|---|---|---|
| Rxxx_Stepcounts | 67 | Nov. 7, 2018 |
| Rxxx_Stepcounts | 88 | Nov. 8, 2018 |
| Rxxx_Stepcounts | 51 | Nov. 9, 2018 |
| Rxxx_Stepcounts | 77 | Nov. 10, 2018 |
| Rxxx_Stepcounts | 78 | Nov. 11, 2018 |
| Rxxx_Stepcounts | 56 | Nov. 12, 2018 |

The raw data collected from the pedometer sensor contains data such as but not limited to objectUniqueID, observationDate, and observationData as in Table. 9. This data is processed by the system 101 to generate the user activity model, which contains time series data on parameters such as but not limited to residentID, Day, Week, Month, Year, and Weekday/Weekend information. A sample of the user activity model is given in Table. 10.

TABLE 10

| resident ID | NoofSteps | Observation Date | Month | WeekdayName | Day of week | week No | Year | WeekEnd |
|---|---|---|---|---|---|---|---|---|
| Rxxx | 31 | Jan. 1, 2019 | 1 | Tuesday | 1 | 1 | 2019 | N |
| Rxxx | 9 | Jan. 4, 2019 | 1 | Saturday | 5 | 1 | 2019 | Y |
| Rxxx | 99 | Jan. 13, 2019 | 1 | Monday | 7 | 2 | 2019 | N |

The user activity model provides insight on movement of the user in terms of number of steps taken on weekly, monthly, yearly, day wise and even weekend, when a query analysis is performed on the user activity model at step 312.

In an algorithmic representation, sum of raw sensor data for "n" number of days is represented as:

$$X\_WRn = XWRd1 + XWRd2 + XWRd3 + \ldots XWRdn$$

Where,

X is input data.

XWRd1 refers to data from the pedometer sensor for day 1

X_WRn is sum of all inputs from the pedometer sensors from day 1 to n days

X_WRn is input to a Feature Engineering function (FE_func) which gives a Featured Engineered Wearable Output (Z_FEWD) which is output of Process 4. Z_FEWD acts as input to Process 5.

$$Z\_FEWD = FE\_func(X\_WRn)$$

Z_FEWD is further processed by the system 101 to generate the user activity model, which is also termed as process 5 data. The user activity model gives information on number of steps.

5) User Activity Model

The system 101 considers the wearable data i.e. number of steps obtained from the pedometer sensor data, in combination with the PIR sensor data and the door sensor data to determine frailty of the user being monitored. By processing the information on the number of steps, the system 101 identifies how much the user walks every day, i.e. during day-time (6.00 am to next day morning 6.00 am. It considers 24 hours. Since the day wise walking steps might subject to outliers and to get a stable data, we aggregate the walking steps on weekly basis.

From the second feature dataset Z_FEWD, the system 101 obtains weekly data of the walking steps by querying for Weekno and Noofsteps data. The system 101 may use the following query to fetch the required data:

Group by WeekNo & NoofSteps

This query gives a resultset with all wearable data with above conditions sorted by WeekNo and NoofSteps the user walked during the week. Sample data is given in Table 11.

TABLE 11

| WeekNo | NoofStepsinWeeks |
|---|---|
| 1 | 572 |
| 2 | 471 |
| 3 | 463 |
| 4 | 316 |
| 5 | 392 |

This resultset is as ResultWeekWiseWalkingSteps

By processing data in the user activity model, the system 101 calculates average number of walking steps in a week as median of the NoofStepsinWeeks feature of the ResultWeekWiseWalkingSteps resultset. Median is selected because it is less susceptible to data noise.

AvgNoWalkingStepsinWeeks=median (ResultWeekWiseWalkingSteps:NoofStepsinWeeks)

Further the system 101 calculates the Total Count of the NoofStepsinWeeks feature of the ResultWeekWiseWalkingSteps resultset as:

TotalCountWalkingStepsinWeeks=count (ResultWeekWiseWalkingSteps:NoofStepsinWeeks)

Further, the system 101 determines how much change has happened in the Walkingsteps of the user on a weekly basis. Based on this information, the system 101 further assesses whether there is a decrease in walking capacity of the user. The system 101 is configured to interpret decrease in the walking capacity (in terms of walking Steps) of the user as a sign of weakness, and in turn as an indication of frailty. The system 101 determines the DecreaseWalkinginSteps as:

DecreaseWalkinginStepsAverageCounts= ResultWeekWiseWalkingSteps:
NoofStepsinWeeks<AvgNoWalkingStepsinWeeks The result is captured in the resultset DecreasedWalkingStepsAverageCounts, and a sample data is given in table 12.

TABLE 12

| WeekNo | NoofStepsinWeeks |
|--------|------------------|
| 1      | 572              |
| 2      | 471              |
| 3      | 463              |
| 4      | 316              |
| 5      | 392              |

The system 101 then calculates the Total Count of the NoofStepsinWeeks feature of the above resultset DecreasedWalkingStepsAverageCounts, as:

Decreased WalkingStepsWeeksCount=count (DecreasedWalkingStepsAverageCounts:NoofStepsinWeeks)

The system 101 then determines, based on pattern of walking count observed from the decreased walking steps count calculated, percentage decrease of the number of walking steps, as:

GetDecreasedWalkingStepsWeeksPercentage=(DecreasedWalkingStepsWeeksCount/TotalCountWalkingStepsinWeeks)*100

Calculated value of GetDecreasedWalkingStepsWeeksPercentage is represented as $Z\_FR5$, and algorithmic representation of calculation of $Z\_FR5$ is given as:

$$Z\_FR5=FR\_WSC(Z\_FEWD)$$

where, FR_WSC is a function, and refers to finding increase in Walking step counts on weekly basis. FR_WSC returns a numerical percentage.

At step 314 the system 101 further assigns weights to each of process 1 data, process 2 data, process 3 data, and process 5 data. The process 1 data, process 2 data, process 3 data, and process 5 data are also referred to as 'data points'. The objective of assigning weightage is to give more specific preference to certain processes, which may be defined as per preference. The weightage values may be considered as hyperparameter values which are subject to change based on one or more factors such as but not limited to Assisted Living environment, Culture, habits of the user being monitored, and Geography of this implementation.

In an embodiment, the weights are assigned as:
Process 1—Room movement—30%
Process 2—Day Time Bedroom Stay—30%
Process 3—Outdoor Home Movement—20%
Process 5—Walking Steps—20%

After assigning the weights, at step 316, the system 101 calculates weighted cumulative percentage for each of the different process data. Further, at step 320, the system 101 compares the cumulative frailty percentage value of the user calculated, at step 318, with a threshold or frailty. At step 322, the system 101 checks if a cumulative frailty percentage value of the user calculated at step 318 exceeds a threshold percentage. Here, value of the threshold percentage is pre-configured, as per requirements. For example, the value of threshold percentage is 40. This threshold of 40% is to be considered as a hyperparameter value, which is subject to change based on the Assisted Living environment, Culture, habits of the user being monitored, and Geography of this implementation and so on.

If during the comparison, the system 101 identifies that the cumulative frailty percentage exceeds the threshold percentage (i.e. 40%), the system 101 interprets that the user is:
spending less time in moving between the rooms
spending more time in Bedroom during the day time
spending less time in moving out of his home
showing a decrease in number of steps The system 101 then validates the assessments made. In order to perform the validation, the system 101 fetches output of the 4 processes:
Process 1 output is stored in GetReducedRoomChangePercentage
Process 2 output is stored in GetIncreasedDaytimeBedroomStayPercentage
Process 3 output is stored in GetReducedDoorMovementPercentage
Process 5 output is stored in GetDecreasedWalkingStepsWeeksPercentage Then the system 101 calculates the cumulative percentage values as:

Cumlative_ReducedRoomChangePercentage= GetReducedRoomChangePercentage*0.30

Cumlative_IncreasedBedroomStayPercentage= GetIncreasedDaytimeBedroomStayPercentage*0.30

Cumlative_ReducedDoorMovementPercentage= GetReducedDoorMovementPercentage*0.20

Cumlative_ReducedWalkingStepsPercentage= GetDecreasedWalkingStepsWeeksPercentage*0.20

Further, value of the cumulative Frailty Percentage is calculated as:

WeightedCumlative_FrailityPercentage= Cumlative_ReducedRoomChangePercentage+Cumlative_IncreasedBedroomStayPercentage+Cumlative_ReducedDoorMovementPercentage+Cumlative_ReducedWalkingStepsPercentage Further, the weighted cumulative frailty percentage is compared with the threshold percentage.

If WeightedCumlative_FrailityPercentage>=40
  Frailty="Y"
Else
  Frailty="N"
i.e. if Cumlative_FrailityPercentage exceeds the threshold value of 40%, it means that the user is showing the indication of Frailty.

Algorithmic representation of frailty detection is given as:
The weighted cumulative percentage is calculated by assignment of weights as:

$$Weigh\_Cum\_FR = 0.30*Z\_FR1 + 0.30*Z\_FR2 + 0.20*Z\_FR3 + 0.20*Z\_FR5$$

If Weigh_Cum_FR>=40
Frailty=Yes (at step 324)
Else:
frailty=No (at step 326)

The system 101 may then communicate to the user or any other authorized person, information on the frailty assessment, using a suitable interface. For example, the system 101 may send an alert (SMS, or an alarm and so on) to the user, and/or to a doctor, and/or to a friend/relative of the user, and so on, as configured. The system 101 may also be configured to store information on results of the frailty assessment performed from time to time, so that the health condition over a time can be compared.

Various steps in method 300 may be performed in the same order as depicted, or in any alternate order possible. In another embodiment, one or more steps in method 300 may be omitted.

Experimental Results

In order to verify effectiveness of the frailty detection being performed by the system 101, a test-set of 9 subjects were selected, and frailty detection was performed using the system 101, during which the system 101 collected various sensor data over a period of time, and performed the frailty analysis based on the collected data. Further, a qualitative analysis was performed by conducting a series of surveys over a period of time falling under the time period during which the sensor data was collected by the system 101 for the frailty detection. Based on the survey results, a frailty index was calculated after each survey, and a change in frailty between the two surveys was calculated, and frailty of the user was determined based on the change in frailty. Table. 13 shows values of different parameters estimated by the system 101 and corresponding frailty index calculated, wherein the frailty index indicates whether the user has frailty or not. Table.14 shows survey results and assessment. Results from Table.13 and Table. 14 when combined, gives indication of accuracy with which the frailty detection was carried out by the system 101.

TABLE 13

| User ID | Time period | Room Movement Reduction | Bedroom Stay Increase | Door Movement Reduction | Frailty percentage | Average frailty percentage | Frailty? |
|---|---|---|---|---|---|---|---|
| 1 | November 2017-July 2018 | 48 | 50 | 49 | 48 | 45 | Y |
|  | August 2018-March 2019 | 47 | 50 | 30 | 42 |  |  |
| 2 | November 2017-July 2018 | 49 | 49 | 0 | 34 | 33 | N |
|  | August 2018-March 2019 | 47 | 49 | 1 | 33 |  |  |
| 3 | November 2017-July 2018 | 48 | 50 | 6 | 36 | 41 | Y |
|  | August 2018-March 2019 | 49 | 50 | 44 | 44 |  |  |
| 4 | November 2017-July 2018 | 47 | 50 | 19 | 39 | 41 | Y |
|  | August 2018-March 2019 | 48 | 49 | 31 | 43 |  |  |
| 5 | November 2017-July 2018 | 47 | 49 | 27 | 41 | 41 | Y |
|  | August 2018-March 2019 | 48 | 50 | 25 | 41 |  |  |
| 6 | November 2017-July 2018 | 48 | 49 | 34 | 44 | 42 | Y |
|  | August 2018-March 2019 | 49 | 49 | 25 | 41 |  |  |
| 7 | November 2017-July 2018 | 49 | 50 | 39 | 46 | 47 | Y |
|  | August 2018-March 2019 | 49 | 49 | 46 | 48 |  |  |
| 8 | November 2017-July 2018 | 49 | 50 | 26 | 42 | 41 | Y |
|  | August 2018-March 2019 | 49 | 49 | 21 | 40 |  |  |
| 9 | November 2017-July 2018 | 47 | 49 | 40 | 45 | 46 | Y |
|  | August 2018-March 2019 | 48 | 50 | 49 | 48 |  |  |

TABLE 14

| Resident ID | Survey 1 Date | Survey 1 Frailty Index | Survey 2 date | Survey 2 Frailty Index | Change in Frailty between two surveys | Frailty change |
|---|---|---|---|---|---|---|
| 1 | April 10, 2018 | 0.315789473684211 | Dec. 27, 2018 | 0.342105263157895 | 0.0263157894736842 | More frail |
| 2 | April 4, 2018 | 0.162162162162162 | Dec. 20, 2018 | 0.297297297297297 | 0.135135135135135 | More frail |
| 3 | March 15, 2018 | 0.108108108108108 | Dec. 13, 2018 | 0.135135135135135 | 0.027027027027027 | More frail |
| 4 | March 21, 2018 | 0.105263157894737 | Dec. 20, 2018 | 0.210526315789474 | 0.105263157894737 | More frail |
| 5 | April 5, 2018 | 0.027027027027027 | Dec. 17, 2018 | 0.0540540540540541 | 0.027027027027027 | More frail |
| 6 | May 16, 2018 | 0.157894736842105 | Dec. 11, 2018 | 0.368421052631579 | 0.210526315789474 | More frail |
| 7 | May 11, 2018 | 0.105263157894737 | Dec. 17, 2018 | 0.105263157894737 | 0 | No change |
| 8 | April 6, 2018 | 0.0789473684210526 | Dec. 18, 2018 | 0.0526315789473684 | −0.0263157894736842 | Less frail |
| 9 | March 21, 2018 | 0.162162162162162 | Dec. 17, 2018 | 0.189189189189189 | 0.027027027027027 | More frail |

The frailty change in Table.14 is measured as:

Value of 'change in frailty'>0: More Frail

Value of 'change in frailty'<0: Less Frail

Value of 'change in frailty'=0: No change

Based on data in Table. 13 and Table. 14, it was identified that the system 101 predicted frailty accurately for 6 out of 9 subjects.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for frailty detection, comprising:

obtaining, via one or more hardware processors, Passive Infrared (PIR) sensor data and door sensor data, from a plurality of PIR sensors and door sensors respectively, positioned at different locations of a building where a user being monitored is located, as a first input, wherein the PIR sensors are installed at selected locations of the building to track user's movement in and out of each room or selected rooms, wherein the door sensors are installed at main door of the building to track the user's movement whenever the user is going out of the building and coming back to the building;

obtaining, via the one or more hardware processors, pedometer data with respect to movement of the user, using one or more pedometer sensors, as a second input, wherein the first input and the second input are obtained simultaneously, wherein the pedometer sensors collect information on counts of steps being taken by the user while the user is moving and the pedometer sensors are present in one or more gadgets configured to be attached to the user, wherein the PIR sensors, the door sensors, the pedometer sensors are configured to communicate with the one or more processors and transmit the information of the counts of steps, and the user's movement to the one or more processors in real-time;

processing the PIR sensor data and the door sensor data in raw form to extract feature data to generate a first feature dataset and further using the first feature dataset to build a room movement data model, a day-time bedroom-stay data model, and an outdoor home movement model, for the user, via the one or more hardware processors, wherein the first feature dataset includes information of room change indicator as Yes or No (Y/N), time difference, weekend/weekday, wherein to track whether the user is moving out of a home, a door location is considered;

wherein the day-time bedroom-stay is determined by querying the first feature dataset to obtain information about "FromLocation", "ToLocation", "RoomchangeInd" and "Time Period" features, wherein the outdoor home movement model provides information on how many times the user goes outside of the home, and outdoor home movement is detected by querying the first feature dataset to get information on the "ToLocation" feature, processing the pedometer sensor data by extracting feature data, to generate a user activity model for the user, via the one or more hardware processors, and a dataset of the user activity model is termed as a second feature dataset, wherein the user activity model contains time series data on parameters including resident identification (ID), day, week, month, year, weekday/weekend, wherein the user activity model includes information on step count of the user and obtains weekly data of the step counts of the user by querying the second feature dataset with a week number and number of steps in the corresponding week number, wherein while processing the pedometer sensor data, the one or more hardware processors assess signs of frailty based on movement of the user within home through a number of steps taken and the user activity model provide insights on movement of the user in terms of the number of steps taken by the user on weekly, monthly, yearly, day wise, and weekend;

assigning weights to data points deduced from the room movement data model, the day-time bedroom stay data model, the outdoor home movement model, and the user activity model, wherein the data points comprises a total count of reduced movement of the user with the room, a total count of instances in which the user was identified as spending increased amount of time inside the bedroom, a percentage decrease in outdoor movement of the user, and a step count of the user over the period of time, wherein the weights are considered as hyperparameter values that are subject to change based on one or more factors including an assisted living environment, culture of the user, habits of the user being monitored, geography of implementation;

calculating a weighted cumulative percentage value for each of the one or more data points, based on the assigned weights and a measured value of each of the data points;

calculating a cumulative frailty percentage value, based on the weighted cumulative percentage value of the data points;

determining that the user has frailty if the cumulative frailty percentage value exceeds a frailty threshold and the one or more hardware processors interprets that the user is spending less time in moving between the rooms, spending more time in Bedroom during the day time, spending less time in moving out of his home, showing a decrease in number of steps, and the user shows an indication of frailty;

communicating information on the frailty to the user or an authorized person using an interface by sending an alert to the user or the authorized person and the one or more hardware processors storing information on results of the frailty assessment performed from time to time to compare health condition of the user over time; and determining a value of change in frailty for the user by conducting multiple surveys at varied dates and the value of the change in frailty greater than zero indicates more frail, the value of the change in frailty less than zero indicates less frail, and the value of the change in frailty equal to zero indicates no change.

2. The method as claimed in claim 1, wherein the room movement data model comprises calculated information on median average room movement, a total room movement count over a pre-defined period of time, change in movement pattern indicating decrease in movement of the user, and total count of reduced movement, wherein the one or more hardware processors determines how much change happened in walking steps of the user on a weekly basis and assess whether there is a decrease in walking capacity of the user, and the one or more hardware processors interprets decrease in the walking capacity as a sign of weakness and considered as an indication of frailty.

3. The method as claimed in claim 2, wherein the change in the movement pattern of the user is determined in terms of the total room movement count below the median average room movement, and a percentage change in room movement, wherein the percentage change in room movement is computed based on number of instances of room movement below the median average room movement and the total room movement count.

4. The method as claimed in claim 1, wherein the daytime bedroom-stay data model comprises calculated information on time spent by the user in the bedroom in seconds, total count of daytime bedroom stays over a period of time, change in bedroom stay pattern indicating increase in amount of time spent in the bedroom by the user, and total count of instances in which the user was identified as spending increased amount of time inside the bedroom during day time.

5. The method as claimed in claim 4, wherein the change in bedroom stay pattern is determined as a percentage change based on number of instances of the bedroom stay exceeding a median average of bedroom stay and instances in which the user was identified as spending increased amount of time inside the bedroom.

6. The method as claimed in claim 1, wherein the outdoor home movement model comprises calculated information on a median average door movement, a total count of door movements, a change in outdoor movement pattern indicating decrease in an outdoor movement of the user, a count of instances in which reduced outdoor movement was detected, and a percentage decrease in outdoor movement of the user.

7. The method as claimed in claim 6, wherein the decrease in the outdoor movement of the user is determined as a percentage change computed based on number of instances of door movement below the median average door movement, and the total count of door movements.

8. A system for frailty detection, the system comprising:
one or more hardware processors;
a communication interface; and
a memory storing a plurality of instructions, wherein the plurality of instructions when executed cause the one or more hardware processors to:
obtain Passive Infrared (PIR) sensor data and door sensor data, from a plurality of PIR sensors and door sensors respectively, positioned at different locations of a building where a user being monitored is located, as a first input, wherein the PIR sensors are installed at selected locations of the building to track user's movement in and out of each room or selected rooms, wherein the door sensors are installed at main door of the building to track the user's movement whenever the user is going out of the building and coming back to the building;
obtain pedometer data with respect to movement of the user, using one or more pedometer sensors, as a second input, wherein the first input and the second input are obtained simultaneously,
wherein the pedometer sensors collect information on counts of steps being taken by the user while the user is moving and the pedometer sensors are present in one or more gadgets configured to be attached to the user,
wherein the PIR sensors, the door sensors, the pedometer sensors are configured to communicate with the one or more processors and transmit the information of the counts of steps, and the user's movement to the one or more processors in real-time;

process the PIR sensor data and the door sensor data in raw form to extract feature data to generate a first feature dataset and further using the first feature dataset to build a room movement data model, a day-time bedroom-stay data model, and an outdoor home movement model, for the user, wherein the first feature dataset includes information of room change indicator as Yes or No (Y/N), time difference weekend/weekday, wherein to track whether the user is moving out of a home, a door location is considered;

wherein the day-time bedroom-stay is determined by querying the first feature dataset to obtain information about "FromLocation", "ToLocation", "RoomchangeInd" and "Time Period" features, wherein the outdoor home movement model provides information on how many times the user goes outside of the home, and outdoor home movement is detected by querying the first feature dataset to get information on the "ToLocation" feature, process the pedometer sensor data by extracting feature data, to generate a user activity model for the user, and a dataset of the user activity model is termed as a second feature dataset, wherein the user activity model contains time series data on parameters including resident identification (ID), day, week, month, year, weekday/weekend, wherein the user activity model includes information on step count of the user and obtains weekly data of the step counts of the user by querying the second feature dataset with a week number and number of steps in the corresponding week number, wherein while processing the pedometer sensor data, the one or more hardware processors assess signs of frailty based on movement of the user within home through a number of steps taken and the user activity model provide insights on movement of the user in terms of the number of steps taken by the user on weekly, monthly, yearly, day wise, and weekend;

assign weights to data points deduced from the room movement data model, the day-time bedroom stay data model, the outdoor home movement model, and the user activity model, wherein the data points comprises a total count of reduced movement of the user with the room, a total count of instances in which the user was identified as spending increased amount of time inside the bedroom, a percentage decrease in outdoor movement of the user, and a step count of the user over the period of time, wherein the weights are considered as hyperparameter values that are subject to change based on one or more factors including an assisted living environment, culture of the user, habits of the user being monitored, geography of implementation;

calculate a weighted cumulative percentage value for each of the one or more data points, based on the assigned weights and measured value of each of the data points;

calculate a cumulative frailty percentage value, based on the weighted cumulative percentage value of the data points;

determine that the user has frailty if the cumulative frailty percentage value exceeds a frailty threshold and the one or more hardware processors interprets that the user is spending less time in moving between the rooms, spending more time in Bedroom during the day time, spending less time in moving out of his home, showing a decrease in number of steps, and the user shows an indication of frailty;

communicate information on the frailty to the user or an authorized person using an interface by sending an alert to the user or the authorized person and the one or more hardware processors storing information on results of the frailty assessment performed from time to time to compare health condition of the user over time; and determine a value of change in frailty for the user by conducting multiple surveys at varied dates and the value of the change in frailty greater than zero indicates more frail, the value of the change in frailty less than zero indicates less frail, and the value of the change in frailty equal to zero indicates no change.

9. The system as claimed in claim 8, wherein the room movement data model comprises calculated information on median average room movement, a total room movement count over a pre-defined period of time, change in movement pattern indicating decrease in movement of the user, and total count of reduced movement, wherein the one or more hardware processors determines how much change happened in walking steps of the user on a weekly basis and assess whether there is a decrease in walking capacity of the user, and the one or more hardware processors interprets decrease in the walking capacity as a sign of weakness and considered as an indication of frailty.

10. The system as claimed in claim 9, wherein the system determines the change in the movement pattern of the user in terms of the total room movement count below the median average room movement, and a percentage change in room movement, wherein the percentage change in room movement is computed based on number of instances of room movement below the median average room movement and the total room movement count.

11. The system as claimed in claim 8, wherein the day-time bedroom-stay data model comprises calculated information on time spent by the user in the bedroom in seconds, total count of daytime bedroom stays over a period of time, change in bedroom stay pattern indicating increase in amount of time spent in the bedroom by the user, and total count of instances in which the user was identified as spending increased amount of time inside the bedroom during day time.

12. The system as claimed in claim 11, wherein the system determines the change in bedroom stay pattern as a percentage change based on number of instances of the bedroom stay exceeding a median average of bedroom stay and instances in which the user was identified as spending increased amount of time inside the bedroom.

13. The system as claimed in claim 8, wherein the outdoor home movement model comprises calculated information on a median average door movement, a total count of door movements, a change in outdoor movement pattern indicating decrease in outdoor movement of the user, a count of instances in which reduced outdoor movement was detected, and a percentage decrease in outdoor movement of the user.

14. The system as claimed in claim 13, wherein the system determines the decrease in the outdoor movement of the user as a percentage change computed based on number of instances of door movement below the median average door movement, and the total count of door movements.

15. A non-transitory computer readable medium for frailty detection, wherein the non-transitory computer readable medium comprising a plurality of instructions, which when executed, cause:

obtaining, via one or more hardware processors, Passive Infrared (PIR) sensor data and door sensor data, from a plurality of PIR sensors and door sensors respectively, positioned at different locations of a building where a user being monitored is located, as a first input, wherein the PIR sensors are installed at selected locations of the building to track user's movement in and out of each room or selected rooms, wherein the door sensors are installed at main door of the building to track the user's movement whenever the user is going out of the building and coming back to the building;

obtaining, via the one or more hardware processors, pedometer data with respect to movement of the user, using one or more pedometer sensors, as a second input, wherein the first input and the second input are obtained simultaneously, wherein the pedometer sensors collect information on counts of steps being taken by the user while the user is moving and the pedometer sensors are present in one or more gadgets configured to be attached to the user, wherein the PIR sensors, the door sensors, the pedometer sensors are configured to communicate with the one or more processors and transmit the information of the counts of steps, and the user's movement to the one or more processors in real-time;

processing the PIR sensor data and the door sensor data in raw form to extract feature data to generate a first feature dataset and further using the first feature dataset to build a room movement data model, a day-time bedroom-stay data model, and an outdoor home movement model, for the user, via the one or more hardware processors, wherein the first feature dataset includes information of room change indicator as Yes or No (Y/N), time difference, weekend/weekday, wherein to track whether the user is moving out of a home, a door location is considered;

wherein the day-time bedroom-stay is determined by querying the first feature dataset to obtain information about "FromLocation", "ToLocation", "RoomchangeInd" and "Time Period" features, wherein the outdoor home movement model provides information on how many times the user goes outside of the home, and outdoor home movement is detected by querying the first feature dataset to get information on the "ToLocation" feature, processing the pedometer sensor data by extracting feature data, to generate a user activity model for the user, via the one or more hardware processors, and a dataset of the user activity model is termed as a second feature dataset, wherein the user activity model contains time series data on parameters including resident identification (ID), day, week, month, year, weekday/weekend, wherein the user activity model includes information on step count of the user and obtains weekly data of the step counts of the user by querying the second feature dataset with a week number and number of steps in the corresponding week number, wherein while processing the pedometer sensor data, the one or more hardware processors assess signs of frailty based on movement of the user within home through a number of steps taken and the user activity model provide insights on movement of the user in terms of the number of steps taken by the user on weekly, monthly, yearly, day wise, and weekend;

assigning weights to data points deduced from the room movement data model, the day-time bedroom stay data model, the outdoor home movement model, and the user activity model, wherein the data points comprises a total count of reduced movement of the user with the room, a total count of instances in which the user was identified as spending increased amount of time inside the bedroom, a percentage decrease in outdoor movement of the user, and a step count of the user over the period of time, wherein the weights are considered as hyperparameter values that are subject to change based on one or more factors including an assisted living environment, culture of the user, habits of the user being monitored, geography of implementation;

calculating a weighted cumulative percentage value for each of the one or more data points, based on the assigned weights and a measured value of each of the data points;

calculating a cumulative frailty percentage value, based on the weighted cumulative percentage value of the data points;

determining that the user has frailty if the cumulative frailty percentage value exceeds a frailty threshold and the one or more hardware processors interprets that the user is spending less time in moving between the rooms, spending more time in Bedroom during the day time, spending less time in moving out of his home, showing a decrease in number of steps, and the user shows an indication of frailty;

communicating information on the frailty to the user or an authorized person using an interface by sending an alert to the user or the authorized person and the one or more hardware processors storing store information on results of the frailty assessment performed from time to time to compare health condition of the user over time; and determining a value of change in frailty for the user by conducting multiple surveys at varied dates and the value of the change in frailty greater than zero indicates more frail, the value of the change in frailty less than zero indicates less frail, and the value of the change in frailty equal to zero indicates no change.

16. The non-transitory computer readable medium as claimed in claim 15, wherein the room movement data model comprises calculated information on median average room movement, a total room movement count over a pre-defined period of time, change in movement pattern indicating decrease in movement of the user, and total count of reduced movement, wherein the one or more hardware processors determines how much change happened in walking steps of the user on a weekly basis and assess whether there is a decrease in walking capacity of the user, and the one or more hardware processors interprets decrease in the walking capacity as a sign of weakness and considered as an indication of frailty.

17. The non-transitory computer readable medium as claimed in claim 16, wherein the change in the movement pattern of the user is determined in terms of the total room movement count below the median average room movement, and a percentage change in room movement, wherein the percentage change in room movement is computed based on number of instances of room movement below the median average room movement and the total room movement count.

18. The non-transitory computer readable medium as claimed in claim 15, wherein the day-time bedroom-stay data model comprises calculated information on time spent by the user in the bedroom in seconds, total count of daytime bedroom stays over a period of time, change in bedroom stay pattern indicating increase in amount of time spent in the bedroom by the user, and total count of instances in which the user was identified as spending increased amount of time inside the bedroom during day time.

19. The non-transitory computer readable medium as claimed in claim 18, wherein the change in bedroom stay pattern is determined as a percentage change based on number of instances of the bedroom stay exceeding a median average of bedroom stay and instances in which the user was identified as spending increased amount of time inside the bedroom.

20. The non-transitory computer readable medium as claimed in claim 15, wherein the outdoor home movement model comprises calculated information on a median average door movement, a total count of door movements, a change in outdoor movement pattern indicating decrease in an outdoor movement of the user, a count of instances in which reduced outdoor movement was detected, and a percentage decrease in outdoor movement of the user.

* * * * *